(12) United States Patent
Tajiri et al.

(10) Patent No.: US 10,718,734 B2
(45) Date of Patent: Jul. 21, 2020

(54) METHOD FOR DETERMINING ANTIRUST EFFECT OF TREATED WATER

(71) Applicant: Toshikogyo Co., Ltd., Yokohama-shi, Kanagawa (JP)

(72) Inventors: Yasuo Tajiri, Yokohama (JP); Mitsuo Ishikawa, Yokohama (JP); Kunio Nemoto, Yokohama (JP); Nobuyuki Kamiya, Yokohama (JP)

(73) Assignee: Toshikogyo Co., Ltd., Kanagawa (JP)

( * ) Notice: Subject to any disclaimer, the term of this patent is extended or adjusted under 35 U.S.C. 154(b) by 342 days.

(21) Appl. No.: 15/809,444

(22) Filed: Nov. 10, 2017

(65) Prior Publication Data
US 2018/0088075 A1    Mar. 29, 2018

Related U.S. Application Data

(62) Division of application No. 14/894,721, filed as application No. PCT/JP2014/002890 on May 30, 2014, now abandoned.

(51) Int. Cl.
*G01N 27/416* (2006.01)
*G01N 33/18* (2006.01)
(Continued)

(52) U.S. Cl.
CPC ......... *G01N 27/416* (2013.01); *G01N 27/30* (2013.01); *G01N 27/4161* (2013.01); *G01N 33/18* (2013.01); *C02F 1/30* (2013.01)

(58) Field of Classification Search
CPC .. G01N 27/416; G01N 33/18; G01N 27/4161; G01N 27/30; C02F 1/30
(Continued)

(56) References Cited

U.S. PATENT DOCUMENTS

| | | | | |
|---|---|---|---|---|
| 4,056,445 A | * | 11/1977 | Gauntt | G01N 17/02 205/775.5 |
| 4,784,729 A | * | 11/1988 | Jasinski | G01N 17/02 205/775.5 |

(Continued)

FOREIGN PATENT DOCUMENTS

| | | |
|---|---|---|
| JP | 638549 A | 1/1988 |
| JP | 432758 A | 2/1992 |
| JP | 2005321275 A | 11/2005 |

OTHER PUBLICATIONS

Ketrane et al. (R. Katrane, B. Saidani, O. Gil, L. Leleyter, F. Baraud, Efficiency of five scale inhibitors on calcium carbonate precipitation from hard water: Effect of temperature and concentration, Desalination, 249 (2009) 1397-1404) (Year: 2009).*

(Continued)

*Primary Examiner* — Maris R Kessel
*Assistant Examiner* — Joshua L Allen
(74) *Attorney, Agent, or Firm* — The Webb Law Firm (57) ABSTRACT

A method of determining an enhancement in rust-prevention of treated water by applying an electric current between a first cathode electrode and an anode electrode, and between a second cathode electrode and the anode electrode, wherein the first cathode electrode, the second cathode electrode, and the anode electrode are immersed in treated water; applying a comparative electric current between a first comparative cathode electrode and a comparative anode electrode, and between a second comparative cathode electrode and the comparative anode electrode, wherein the first comparative cathode electrode, the second comparative cathode electrode, and the at least one comparative anode electrode are immersed in untreated water; and determining an antirust effect of the treated water based on a first potential difference across the first cathode electrode and the second cathode (Continued)

electrode, and a second potential difference across the first comparative cathode electrode and the second comparative cathode electrode.

11 Claims, 5 Drawing Sheets

(51) Int. Cl.
   *G01N 27/30* (2006.01)
   *C02F 1/30* (2006.01)
(58) Field of Classification Search
   USPC ........................................ 204/404; 205/775.5
   See application file for complete search history.

(56) References Cited

U.S. PATENT DOCUMENTS

| | | | | |
|---|---|---|---|---|
| 4,840,719 A | * | 6/1989 | Jasinski | G01N 17/02 134/42 |
| 4,863,572 A | * | 9/1989 | Jasinski | G01N 17/02 205/775.5 |
| 6,683,463 B2 | * | 1/2004 | Yang | G01N 17/02 204/404 |
| 7,309,414 B2 | * | 12/2007 | Yang | G01N 17/02 204/404 |
| 7,466,149 B1 | * | 12/2008 | Yang | G01N 17/02 204/404 |
| 2009/0123340 A1 | * | 5/2009 | Knudsen | G08B 21/12 422/105 |

OTHER PUBLICATIONS

Alencar de Souza et al. (EAd Souza, JAdCP Gomes, Influence of Electrochemical Water Treatment on Carbon Steel Corrosion, Int. J. Electrochm. Sci., 9 (2014) 206-219 (Year: 2014).*

Chao et al. (Y Chao, O Homer, F Hui, J Ledion, H Perrot, Direct detection of calcium carbonate scaling via a pre-calcified sensitive area of a quartz crystal microbalance, Desalination 352 (2014) 103-108) (Year: 2014).*

Powell et al. (ST Powell, HE Bacon, EL Knoedler, Corrosion prevention by controlled calcium carbonate scale, Industrial and Engineering Chemistry, 40(3) (1948) 453-457) (Year: 1948).*

"Introduction of the Products" in the website of Toshikogyo Co, LTD. whose URL is http://www.biowater.co.jp/product/feature.html (searched on Apr. 21, 2014).

Ketrane et al., "Efficiency of five scale inhibitors on calcium carbonate precipitation from hard water: Effect of temperature and concentration", Desalination, 2009, pp. 1397-1404, vol. 249.

* cited by examiner

METHOD FOR DETERMINING ANTIRUST EFFECT OF TREATED WATER

CROSS-REFERENCE TO RELATED APPLICATION

This application is a divisional application of U.S. application Ser. No. 14/894,721 filed Nov. 30, 2015, which is the United States national phase of International Application No. PCT/JP2014/002890 filed May 30, 2014, the disclosure of which is hereby incorporated in its entirety by reference.

BACKGROUND OF THE INVENTION

Technical Field

The present invention relates to a determination device for determining antirust effect of treated water and a method for determining antirust effect of treated water. More particularly, the present invention relates to a determination device capable of determining, easily and in a short time, an enhancement in rust-prevention of treated water as a result of the treatment, and to a method for determining antirust effect of treated water.

Background Art

In general, when a metal piece is immersed in water for a long time, the surface of the metal piece becomes corroded. Metal corrosion is caused by localized polarization of a part of the surface into an anode and a cathode. A small amount of electric current flows between the anode and the cathode, which causes an oxidation reaction at the anode and a reduction reaction at the cathode. The oxidation reaction at the anode oxidizes the surface of the metal piece, whereby the metal corrosion progresses.

Various kinds of water treatment devices capable of purifying water with ceramics that emits far-infrared rays have been conventionally known as water treatment devices. An example of the water treatment devices may be a device named "THE BIOWATER" (registered trademark), which is sold on market by TOSHIKOGYO CO., LTD. (see Non-patent document 1). It is reported that water treated with this device has various advantages. Especially noticeable is its effectiveness in preventing deterioration caused by red rust. More particularly, metal corrosion progresses more slowly in water treated with this water treatment device than in untreated water. In other words, the treatment of water with the water treatment device enhances antirust effect of water. When the water treatment device is installed, for example, in the piping, through which the water treated with the water treatment device is made to pass, the progress of metal corrosion on the inner surface of the piping is capable of being controlled.

It normally takes a time period from a few months to several years to assess the progress of metal corrosion by observing and analyzing the surface of metal pieces immersed in water. Conventionally, it also takes a time period from a few months to several years from the installation of a water treatment device in a piping to determine the effectiveness of the device in controlling metal corrosion on the inner surface of the piping. Thus, currently it is not possible to determine an improvement in the rust-prevention of treated water within a short time period from the installation.

Also, in general, a water treatment device is usually placed in a piping of large facilities such as factories and buildings. When the piping in which a water treatment device is installed is examined and the effectiveness in treating water with the water treatment device is determined, it is necessary to temporarily stop operation of the equipment provided with the device, to drain water from the piping, and then to observe the inner surface of the piping. However, it is often practically difficult to stop operation of the equipment and it requires prodigious labor to drain water from the piping. Thus it is difficult to check whether the anti-corrosion performance of water is enhanced owing to the installment of a water treatment device by examining the piping in which the water treatment device is installed.

PRIOR ART DOCUMENTS

Patent Documents

Non-patent Document 1: "Introduction of the Products" in the website of TOSHIKOGYO CO, LTD. whose URL is http://www.biowater. co.jp/product/feature.html (searched on Apr. 21, 2014).

SUMMARY OF THE INVENTION

Problems to be Solved by the Invention

The objective of the present invention is to provide a determination device for determining antirust effect of treated water, capable of determining, easily and in a short time, an enhancement in anti-corrosion performance of water treated with a water treatment device, and a method for determining antirust effect of the treated water.

Means to Solve the Problems

Means to achieve the objective are as follows:
(1) A determination device for determining antirust effect of treated water comprising a first potential difference measurement device and a second potential difference measurement device, each of which includes:
  at least one anode electrode,
  a pair of cathode electrodes,
  a first current generator for applying an electric current between the anode electrode and a first cathode electrode of the pair of cathode electrodes,
  a second current generator for applying an electric current between the anode electrode and a second cathode electrode of the pair of cathode electrodes,
  an electric current changer for periodically changing a magnitude of an electric current between the first cathode electrode and the second cathode electrode,
  a measurement and output device for measuring a potential difference across the first cathode electrode and the second cathode electrode,
    wherein the at least one anode electrode and the pair of cathode electrodes of the first potential difference measurement device are immersed in treated water that has been treated with a water treatment device, and the at least one anode electrode and the pair of cathode electrodes of the second potential difference measurement device are immersed in untreated water that has not been treated with a water treatment device, and
  a determiner for determining antirust effect of the treated water based on an output signal A outputted by the measurement and output device of the first potential difference measurement device and an output signal B outputted by the measurement and output device of the second potential difference measurement device.

(2) The determination device according to item (1), each of the first and second potential difference measurement devices further including a third current generator for applying an electric current between the first cathode electrode and the second cathode electrode.

(3) The determination device according to item (1) or (2), wherein the determiner determines the antirust effect of the treated water based on a ratio of a level of the output signal A to a level of the output signal B.

(4) The determination device according to any one of items (1)-(3), wherein the pair of the cathode electrodes has a surface made of silver and the anode electrode has a surface made of platinum.

(5) The determination device according to any one of items (1)-(4), wherein the water treatment device contacts water with a hybrid ceramic which emits far-infrared rays having wavelengths from 4.4 µm to 15.4 µm at an integral emissivity of 92% or more.

(6) A method for determining antirust effect of treated water comprising:

applying an electric current between a first cathode electrode of a pair of cathode electrodes and at least one anode electrode, and between a second cathode electrode of the pair of cathode electrodes and the anode electrode, wherein the first cathode electrode, the second cathode electrode, and the anode electrode are immersed in treated water that has been treated with a water treatment device;

applying an electric current between a first comparative cathode electrode of a pair of comparative cathode electrodes and at least one comparative anode electrode, and between a second comparative cathode electrode of the pair of comparative cathode electrodes and the comparative anode electrode, wherein the first comparative cathode electrode, the second comparative cathode electrode, and the comparative anode electrode are immersed in untreated water that has not been treated with a water treatment device; and determining antirust effect of the treated water based on a first potential difference across the first cathode electrode and the second cathode electrode, and a second potential difference across the first comparative cathode electrode and the second comparative cathode electrode.

(7) The method according to item (6), wherein the antirust effect of the treated water is determined based on a ratio of the first potential difference to the second potential difference.

(8) The method according to item (6) or (7), wherein the pair of cathode electrodes and the pair of comparative cathode electrodes have a surface made of silver, and the anode electrode and the comparative anode electrode have a surface made of platinum.

(9) The method according to any one of items (6)-(8), wherein the water treatment device contacts water with a hybrid ceramic which emits far-infrared rays having wavelengths from 4.4 µm to 15.4 µm at an integral emissivity of 92% or more.

Advantages of the Invention

According to the present invention, the cathode reaction is capable of being expedited by the application of an electric current between the anode electrode and the cathode electrodes. Thus the formation of a calcium carbonate film on the cathode electrodes progresses so quickly that a difference between the rust-prevention of the treated water and that of the untreated water can be determined even if a short time is expended on the experiment. Thanks to this invention, researchers no longer have to conduct experiments that involve immersing metal pieces in water for a long time, from months to years. The present invention provides a determination device for determining antirust effect of treated water and a method for determining antirust effect of treated water, capable of determining an improvement in rust-prevention of water by a short-term experiment that requires only several days.

Also, the determination device for determining antirust effect of treated water and the method for determining antirust effect of treated water according to the present invention are capable of determining antirust effect of treated water by utilizing a potential difference across the two electrodes of a pair of cathode electrodes. This is a simple method that does not include actual observation of the surface of a metal piece immersed in the water.

DESCRIPTION OF THE INVENTION

The determination device for determining antirust effect of treated water according to the present invention has a first potential difference measurement device, a second potential difference measurement device, and a determiner. We will explain the first potential difference measurement device in the following, referring to FIG. 1. It should be noted that the second potential difference measurement device has the same structure as the first potential difference measurement device shown in FIG. 1.

Figure 1:
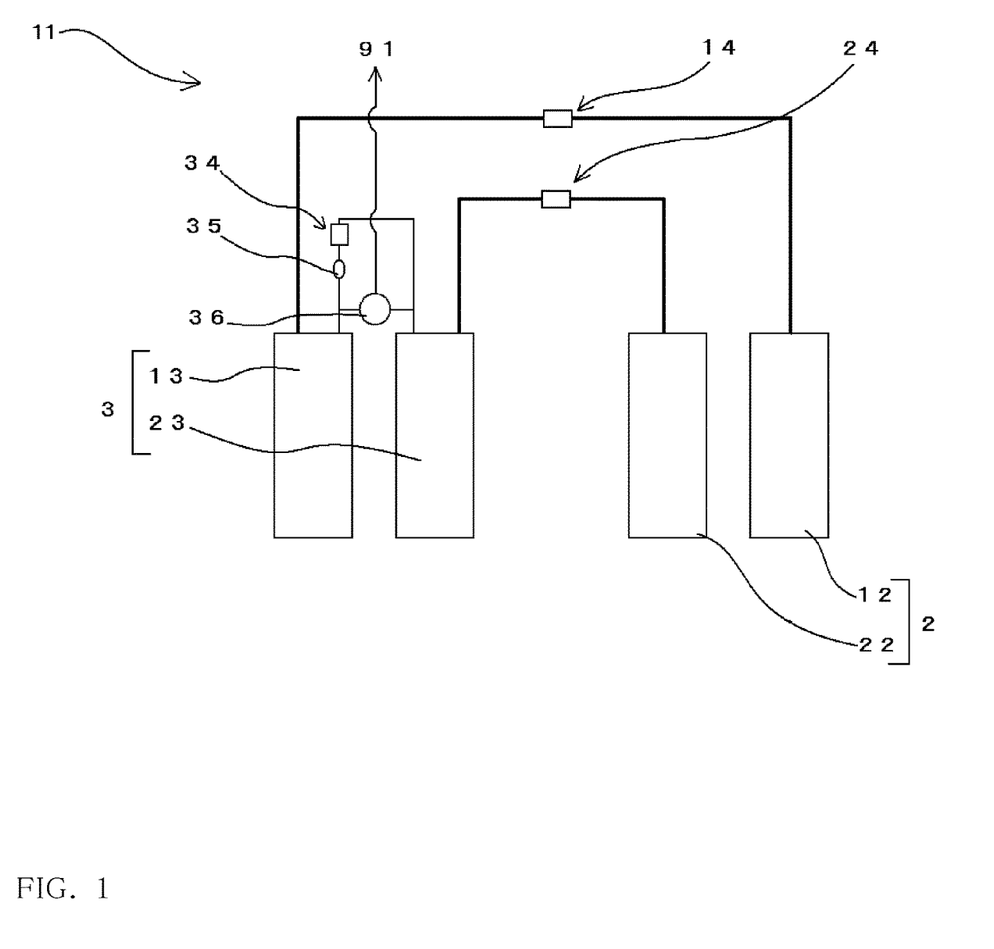
FIG. 1 is a schematic illustration showing the structure of a first potential difference measurement device.

As shown in FIG. 1, the first potential difference measurement device 11 includes at least one anode electrode 2, a pair of cathode electrodes 3, a first current generator 14 for applying an electric current between the at least one anode electrode 2 and a first cathode electrode 13 of the pair of cathode electrodes, and a second current generator 24 for applying an electric current between the at least one anode electrode 2 and a second cathode electrode 23 of the pair of cathode electrodes. The at least anode electrode 2 of the example shown in FIG. 1 is comprised of two anode electrodes. A first anode electrode 12 of the two anode electrodes is connected with the first cathode electrode 13 and a second anode electrode 22 thereof with the second cathode electrode 23.

When the first current generator 14 and the second current generator 24 are activated after the at least one anode electrode 2 and the pair of cathode electrodes 3 are immersed in water, a first electric current flows between the first anode electrode 12 and the first cathode electrode 13, and a second electric current flows between the second anode electrode 22 and the second cathode electrode 23. These first and second electric currents respectively cause an anode reaction at the anode electrodes 2 and a cathode reaction at the cathode electrodes 3.

There is no special limitation on the shape of the anode electrodes; they may be in the shape of a plate, a rod, or a wire.

The anode reaction is generally an oxidation reaction. When the surface of the anode electrode 2 is made of a metal with a small ionization tendency, such as Pt, the reaction represented by formula (1) is mainly caused at the anode electrode. On the other hand, when the surface of the anode electrode 2 is made of a metal with a relatively large ionization tendency, such as Cu, the reaction represented by formula (2) is mainly caused.

$$2H_2O \rightarrow O_2 + 4H^+ + 4e^- \quad (1)$$

$$Cu \rightarrow Cu^{2+} + 2e^- \quad (2)$$

The reaction represented by formula (2) dissolves the metal of which the anode electrode 2 is made. When the metal is dissolved into water, impurities in the water increase. The increased impurities hamper the anode reaction and the cathode reaction, which may, in turn, interfere with accurate determination of the antirust effect of treated water. Thus, the surface of the anode electrode 2 should preferably be made of a metal with a small ionization tendency so that the metal of the anode electrode 2 will not be dissolved into water by electrolysis. Specifically, electrodes known as insoluble electrodes may be used as the anode electrode 2. More specifically, electrodes whose surface is covered with films of platinum or iridium oxide may be used as the anode electrode 2. Electrodes covered with films of platinum or iridium oxide may be produced by plating the surface of a base for electrodes made of other metals such as titanium with platinum or by baking iridium oxide on the surface.

The cathode reaction is generally a reduction reaction. For example, a reaction represented by formula (3) or (4) may be caused.

$$O_2 + 2H_2O + 4e^- \rightarrow 4OH^- \quad (3)$$

$$2H_2O + 2e^- \rightarrow 2OH^- + H_2 \quad (4)$$

The hydroxide ions $OH^-$ produced in the reaction represented by formula (3) or (4) raise the pH of the water surrounding the cathode electrodes 3. When the pH becomes high, $CO_3^{2-}$ ions are prone to be released from carbon dioxide gas that is dissolved in the water. Then calcium ions $Ca^{2+}$ and $CO_3^{2-}$ are prone to react with each other in the water, which produces $CaCO_3$. As a result, as the cathode reaction progresses, a film of $CaCO_3$, which may be called "calcium carbonate" hereinafter", is formed on the surface of the cathode electrodes 3.

The calcium carbonate can have a crystal structure of aragonite or of calcite. The aragonitic crystals are known to be in the form of needles, while the calcitic crystals are known to be in the form of granules. Calcium carbonate with a higher proportion of aragonitic crystals adheres to the cathode electrodes in such a manner that needle-like crystals adhere to the electrodes with many gaps between the needles. As a result, the surface of the electrodes is sparsely covered with films of calcium carbonate. On the other hand, calcium carbonate with a higher proportion of calcitic crystals adheres to the cathode electrodes in such a manner that granular crystals closely adhere to the electrodes, with no space left. Thus the surface of the electrodes is uniformly covered with a film of calcium carbonate without gaps. The larger the area of the surface of the cathode electrodes 3 covered with films of calcium carbonate is, the more increased the electrical resistance of the cathode electrodes 3 is. Therefore films of calcium carbonate with a higher proportion of calcitic crystals closely adhere to the surface of the cathode electrodes 3, without gaps between the films, compared with films of calcium carbonate with a higher proportion of aragonitic crystals, even if the mass of the former is the same as that of the latter. Thus, the former increases the electrical resistance of the surface of the electrodes more than the latter.

When a metal piece is immersed in water, films of calcium carbonate are formed on the surface of the metal piece by the cathode reaction. The calcium carbonate films serve as a protective film for the surface of the metal piece, which controls oxidation of the surface. Also, when the surface of the metal piece is covered with films of calcium carbonate, it is hard for an electric current to flow between an anode and a cathode caused by localized polarization of the surface. As a result, oxidation of the metal surface caused by the anode reaction is controlled. Therefore as films of calcium carbonate adhere to the metal surface more closely without gaps, it is more capable of controlling corrosion of metals.

The surface of the cathode electrodes 3 may be made of materials that are publicly known and used as materials for the negative electrode of electrolytic apparatuses. Specifically, the surface of the cathode electrodes 3 may be made of a metal or alloy with a small ionization tendency, or a metal or alloy excellent in corrosion resistance. More specifically, the surface of the cathode electrodes 3 may be made of silver or copper. Cathode electrodes 3 whose surface is covered with silver or copper may be produced by preparing cathode electrodes that are made of silver or copper in their entirety or by plating the outer surface of a base for electrodes made of other metals with silver or copper.

The first current generator 14 applies a first electric current between the first anode electrode 12 and the first cathode electrode 13. The second current generator 24 applies a second electric current between the second anode electrode 22 and the second cathode electrode 23. Each of the first current generator 14 and the second current generator 24 may be a device for providing an electric current of a constant magnitude. Alternatively, it may be a device that is controlled to periodically change the magnitude of an electric current to be provided. The product of the multiplication of the magnitude of the electric current applied by the first current generator 14 by the time period of the application of the electric current, which product may be called a "quantity of electricity" hereinafter, should preferably be almost the same as the quantity of electricity applied by the second current generator 24. For example, when the first current generator 14 and the second current generator 24 are operated for one hour, the value of the current applied by the first current generator 14 may be set to 4.5 µA and the value of the current applied by the second current generator 24 may be set to 3.5 µA for the first half of the time period, while the current value of the first current generator may be 3.5 µA and the current value of the second current generator may be 4.5 µA for the latter half of the period. Thus the quantity of electricity generated by the first current generator 14 may be adjusted to the same as that generated by the second current generator 24 after one hour's operation of the generators.

There is no special limitation on the first current generator 14 and the second current generator 24, as long as the generators are capable of generating electric currents. Commercial power supplies may be used for this purpose. Also, a single power supply may be used for both of the first current generator 14 and the second current generator 24.

Figure 3:
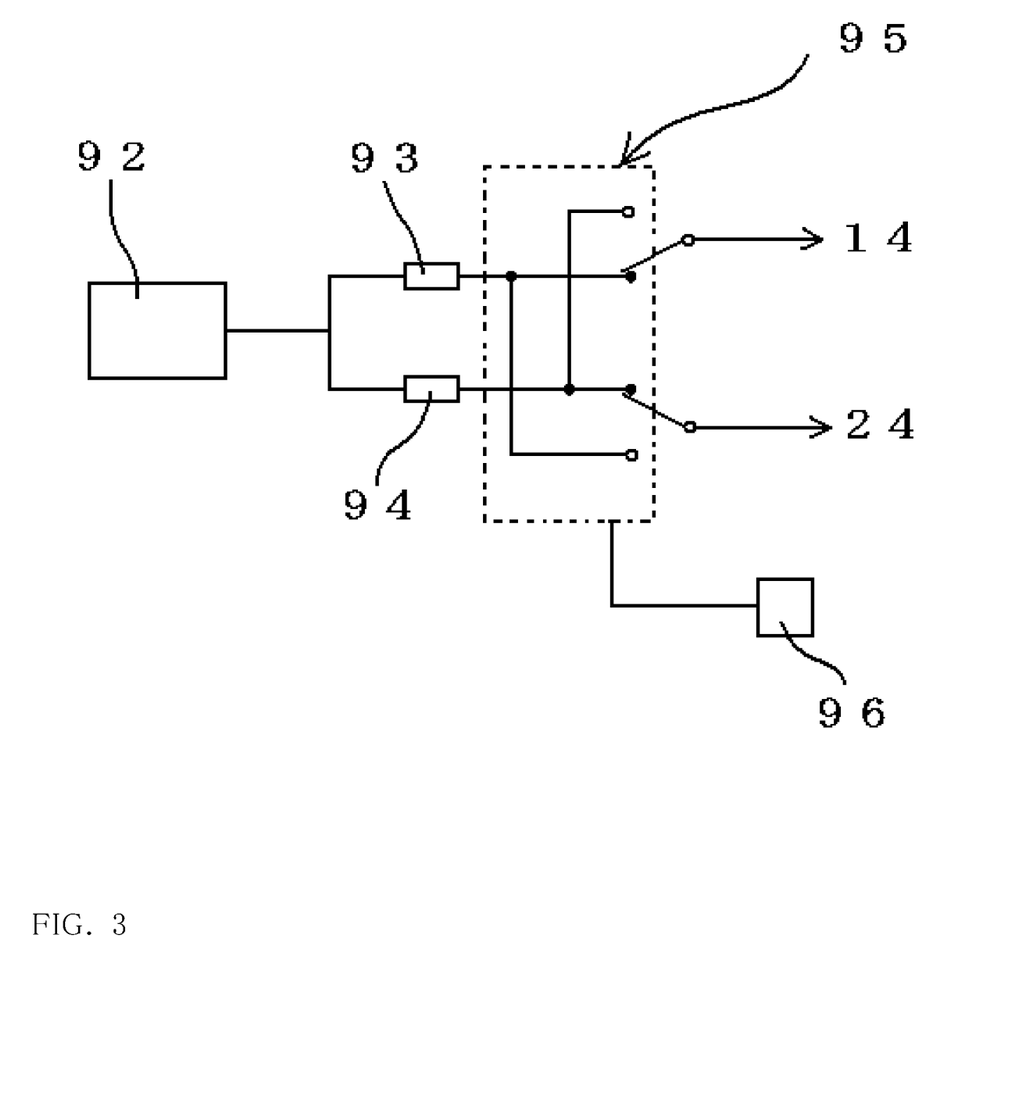
FIG. 3 is a schematic circuit diagram of a control unit for the first and second current generators.

As shown in FIG. 3, for example, the device may be provided with a single power supply 92 for both of the first current generator 14 and the second current generator 24, and further provided with two current transducers 93 and 94 downstream of the power supply 92. The power circuit should be so designed that the first current transducer 93 and the second current transducer 94 send electric currents respectively to the first current generator 14 and the second current generator 24. Specifically, the power circuit should be provided with a control circuit 95 which controls the current transducers in such a manner that the first current transducer 93 sends electric currents to one of the first current generator 14 and second current generator 24, and the second current transducer 94 sends electric currents to the other of the first current generator 14 and second current generator 24. The power circuit should further be provided with a flip-flop controller 96 capable of switching a flow path of the output electric current at regular intervals between a path from the first current transducer 93 to one of the first current generator 14 and second current generator 24 and a path from the second current transducer 94 to the other of the first current generator 14 and second current generator 24. Although there is no limitation on the frequency at which the flow path is switched by the flip-flop controller 96, the flow path should be switched at a frequency from approximately once every five minutes to approximately once an hour.

The larger the magnitude of the electric current applied by the first current generator 14 and the second current generator 24 is, the more rapidly the cathode reaction is caused. This rapid cathode reaction means that the time period necessary for the determination is decreased. On the other hand, if the electric current applied by the first current generator 14 and the second current generator 24 is too large, there is a danger that the user receives an electric shock when s/he touches the electrodes. Also, hydrogen gas vigorously produced at the cathode electrodes may deprive the cathode electrodes of the calcium carbonate films. Therefore the current density applied by the first current generator 14 and the second current generator 24 should be approximately from 10 µA/cm$^2$ to 200 µA/cm$^2$.

The at least one anode electrode 2 may be comprised of one anode electrode or several anode electrodes. The number of the at least one anode electrode 2 should preferably be the same as that of cathode electrodes 3.

The first potential difference measurement device 11 has an electric current changer 35 and a measurement and output device 36, as shown in FIG. 1. The device may further include a third current generator 34.

The third current generator 34 applies an electric current between the first cathode electrode 13 and the second cathode electrode 23. The electric current changer 35 changes the magnitude of the electric current flowing through the pair of cathode electrodes at regular intervals. Although there is no limitation on the frequency at which the magnitude of the electric current is changed by the electric current changer 35, the magnitude should be changed at a frequency approximately from once every five minutes to once an hour.

Any generator may be employed as the third current generator 34, as long as it is capable of applying a constant magnitude of an electric current. Commercial constant current sources may be used as the third current generator 34.

This third current generator 34 may be operated while the first current generator 14 and the second current generator 24 are being operated. When the third current generator 34 and the first and second current generators 14, 24 are operated simultaneously, the magnitude of the electric current applied by the first current generator 14 should be the same as that of the electric current applied by the second current generator 24. Also, the magnitude of the electric current applied by the third current generator 34 should preferably be smaller than that of the electric current applied by the first current generator 14 and that of the electric current applied by the second current generator 24. When the electric currents applied by the first, second and third current generators satisfy this relationship, the cathode reaction always occurs at the first cathode electrode 13 and the second cathode electrode 23. When the third current generator 34 is operated while the first current generator 14 and the second current generator 24 are kept operating in such a manner that they generate a same magnitude of an electric current, the magnitude of the electric current flowing through the first cathode electrode 13 and that of the electric current flowing through the second cathode electrode 23 may be controlled by controlling the direction and magnitude of an electric current applied between the pair of cathode electrodes by the third current generator 34. Therefore the employment of the third current generator 34 enables the user to control the electric current flowing through the pair of cathode electrodes only by controlling the electric current applied by the third current generator 34 without controlling the electric current applied by the first current generator 14 and that applied by the second current generator 24.

Alternatively, only the third current generator 34 may be activated after the first current generator 14 and the second current generator 24 are stopped.

The measurement and output device 26 measures a potential difference across the first cathode electrode 13 and the second cathode electrode 23, and outputs and sends the measured potential difference to a determiner 91. When the potential difference is measured, either the first cathode electrode 13 or the second cathode electrode 23 is used as reference electrode and the other is used as working electrode.

Application of a voltage is necessary to enable the third current generator 34 to pass an electric current through the first cathode electrode 13 and the second cathode electrode 23. A voltage necessary to drive an electric current of a constant magnitude is in proportion to the electrical resistance of the cathode electrodes 3. As explained hereinbefore, the more calcium carbonate films are formed on the surface of the cathode electrodes and the higher the proportion of calcitic crystals in the calcium carbonate films is, the larger the electrical resistance of the cathode electrodes 3 is.

As another method of measuring the electrical resistance of the cathode electrodes 3, a constant-voltage supply for applying a constant voltage may be used as the third current generator 34 and then the magnitude of an electric current flowing through the first cathode electrode 13 and the second cathode electrode 23 may be measured with the measurement and output device 36. Thus this method also works for this invention.

Figure 2:
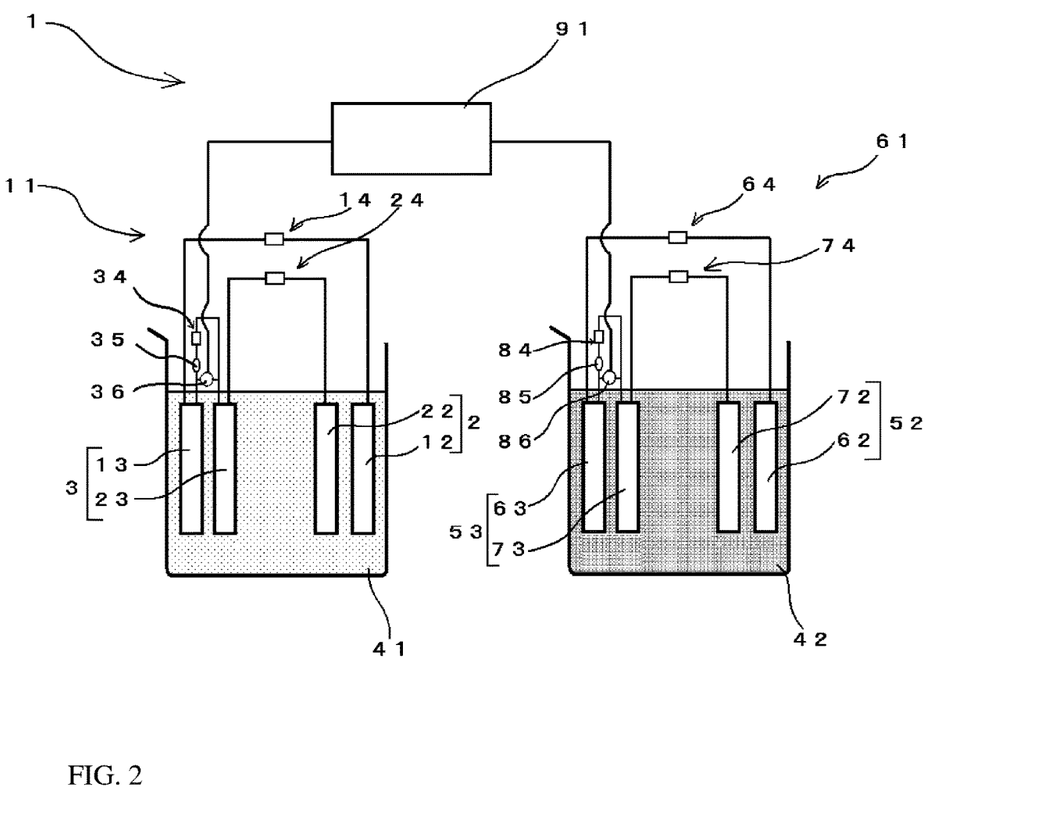
FIG. 2 is a schematic illustration showing the structure of a determination device for determining antirust effect of treated water according to the present invention.

As shown in FIG. 2, the first potential difference measurement device 11 is used for treated water 41 that has been treated with a water treatment device, while a second potential difference measurement device 61 is used for untreated water 42. More specifically, when the determination device for determining antirust effect of treated water according to the present invention is used, the at least one anode electrode 2 and the cathode electrodes 3 of the first potential difference measurement device 11 are immersed in the treated water 41, while at least one comparative anode electrode 52 and comparative cathode electrodes 53 are immersed in the untreated water 42.

The water treatment device may include those having a hybrid ceramic placed in a piping, such as "THE BIOWATER" (registered trademark), which is manufactured by TOSHIKOGYO CO., LTD. The hybrid ceramic is one which emits far-infrared rays having wavelengths from 4.4 μm to 15.4 μm at an integral emissivity of 92% or more. Water treated with this device is improved in at least one of a capability to activate life, bacteriostatic capability, antioxidative capability, detergent ability, environmental cleanup capability, treated condition-sustaining capability, and anticorrosion property (see Non-patent document 1).

Treated water 41 that has been treated with a water treatment device has enhanced rust-prevention, compared with untreated water 42. In other words, a metal piece immersed in treated water 41 has a smaller rate of corrosion than a metal piece immersed in untreated water 42.

Specifically, the cathode reaction tends to form calcium carbonate crystals abundant in calcitic crystals on the surface of a metal piece that is immersed in treated water 41. As a result, the surface of the metal piece is covered with films of calcium carbonate all over. The films control progress of the corrosion. On the other hand, the cathode reaction tends to form calcium carbonate crystals including a high proportion of aragonitic crystals on the surface of a metal piece that is immersed in untreated water 42. As a result, the surface of the metal piece is sparsely covered with films of calcium carbonate. The metal piece begins to corrode at the portions that are not covered with the calcium carbonate films and the corrosion is likely to further proceed.

In FIG. 2, films of calcium carbonate with a high proportion of calcitic crystals are likely to be formed on the cathode electrodes 3 immersed in treated water 41, compared with those formed on the comparative cathode electrodes 53 immersed in untreated water 42. Thus the electrical resistance of the cathode electrodes 3 becomes larger than that of the comparative cathode electrodes 53. Consequently, as the cathode reaction progresses, the voltage necessary to make a constant magnitude of an electric current pass through the first cathode electrode 13 and the second cathode electrode 23 becomes larger than the voltage necessary to make the same magnitude of an electric current pass through the first comparative cathode electrode 63 and the second comparative cathode electrode 73.

The determiner 91 is capable of determining antirust effect of treated water 41 based on an output signal A and an output signal B. There is no special limitation on the kinds of the output signals A and B, as long as the signals serve the functions required by the present invention. For example, the potential difference across the first cathode electrode 13 and the second cathode electrode 23, the value of the electric current passing through the first cathode electrode 13 and the second cathode electrode 23, or the electrical resistance of the cathode electrodes 3 may be used as the output signal A. The output signal B should be a signal of the same kind as the output signal A. For example, when the output signal A is the potential difference across the first cathode electrode 13 and the second cathode electrode 23, the output signal B should be the potential difference across the first comparative cathode electrode 63 and the second comparative cathode electrode 73.

The determiner 91 is capable of determining antirust effect of treated water 41 based on the output signal A and the output signal B. Specifically, the determiner 91 calculates the ratio of the output signal A to the output signal B, the ratio of the output signal B to the output signal A, or the difference between the output signal A and the output signal B, based on which the antirust effect is determined. Let the case where the output signals A and B are potential differences across the respective pairs of cathode electrodes be taken as an example. When the output signal A is larger than the output signal B, the cathode electrodes 3 immersed in treated water 41 is considered to have a surface a larger area of which is covered with films of calcium carbonate including a high proportion of calcitic crystals than the comparative cathode electrodes 53 immersed in untreated water 42 have. Thus when the determiner 91 finds that the output signal A is larger than the output signal B, the determiner determines that the examined water has been treated to a water in which metal pieces are not easily corroded, or the rust-prevention of the treated water is enhanced.

A conventionally known device may be used as the electric current changer 35. The measurement and output device 36 may be a combination of a device for measuring electrical values such as the potential difference across one cathode electrode and the other cathode electrode of a pair of cathode electrodes, and an output device for outputting and sending measured results to the determiner 91.

The operation of the device will be explained hereinafter.

Figure 4:
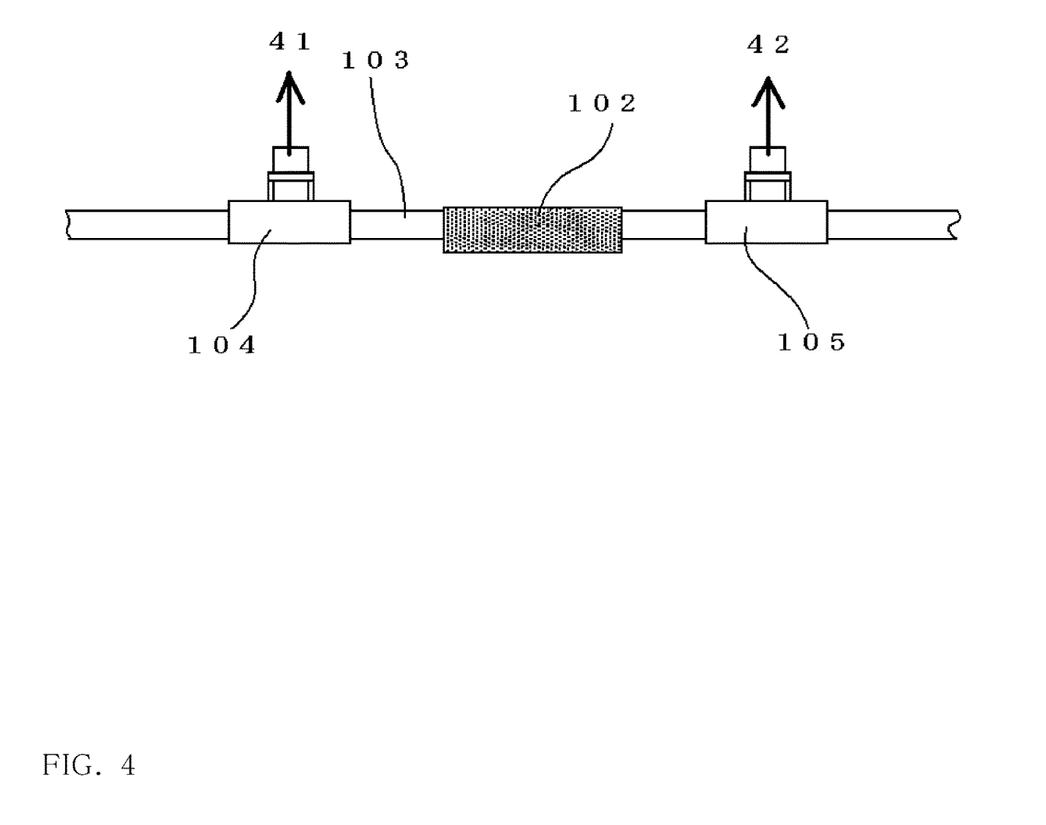
FIG. 4 is a schematic illustration showing an example of how the water treatment device is installed in a piping.

Facilities suppliers would sometimes like to check whether water in a piping is treated and whether metal on the inner surface of the piping is kept from corroding by installing a water treatment device 102, such as "THE BIOWATER (registered trademark)", in the piping in such a manner as shown, for example, in FIG. 4. On such occasions, facilities suppliers may use the determination device for determining antirust effect of treated water according to the present invention. The operation method of this device will be explained in the following: First, untreated water 42 in the piping is sampled through a three-way valve 104 that is fixed to the piping at a place upstream of the water treatment device 102. Treated water 41 is also sampled through a three-way valve 105 that is fixed to the piping at a place downstream of the water treatment device 102. The samples are collected in vessels such as beakers. As shown in FIG. 2, the cathode electrodes 3 and anode electrodes 2 of the first potential difference measurement device 11 are immersed in the treated water 41 in one vessel, and the comparative cathode electrodes 53 and comparative anode electrodes 52 of the second potential difference measurement device 61 are immersed in the untreated water 42 in another vessel.

Then, the first current generators 14 and 64, and the second current generators 24 and 74 are activated to make electric currents pass through the first cathode electrode 13 and the second cathode electrode 23 and through the first comparative cathode electrode 63 and the second comparative cathode electrode 73 respectively. The electric currents cause the cathode reaction respectively at the cathode electrodes 13, 23 and at the comparative cathode electrodes 63, 73, on the surface of which films of calcium carbonate are formed. For example, when electric currents are applied by the first current generator 14 and the first current generator for comparison 64 at a current density from about 10 μA/cm$^2$ to 200 μA/cm$^2$ for about 5 to 500 hours, films of calcium carbonate are formed on the surface of the cathode electrodes 13, 23, 63, and 73 to such a degree that the antirust effect of the treated water 41 is determined. Also, when the hardness of the treated water 41 and that of the untreated water 42 are increased, it serves to reduce the time period for which electric currents are applied. If an increase in the hardness of the treated and untreated waters is desired, the addition of a salt, such as calcium carbonate, would suffice for the purpose. For an accurate determination of the antirust effect, the salt to be added to the treated water 41 should be the same as that to be added to the untreated water 42 in the kind and quantity.

The treated water 41 has enhanced rust-preventive property compared with the untreated water 42. Calcium carbonate crystals abundant in calcitic crystals are more easily precipitated out at the cathode electrodes 3 immersed in the treated water 41 than at the comparative cathode electrodes 53 immersed in the untreated water 42. Thus the surface of the cathode electrodes 3 is covered with films of calcium carbonate all over, compared with the surface of the comparative cathode electrodes 53.

The third current generators 34 and 84 are further activated, while the first current generators 14, 64 and the second current generators 24, 74 are being kept driving. The third current generator 34 makes a constant magnitude of an electric current pass through the first cathode electrode 13 and the second cathode electrode 23, and the third current generator for comparison 84 makes a constant magnitude of an electric current pass through the first comparative cathode electrode 63 and the second comparative cathode electrode 83, wherein the electric currents are adjusted so that the former constant magnitude is the same as the latter constant magnitude. Furthermore, the magnitude of the electric current applied by the first current generator 14 should be the same as that of the electric current applied by the first current generator for comparison 64, and the magnitude of the electric current applied by the second current generator 24 should be the same as that of the electric current applied by the second current generator for comparison 74. Moreover, the magnitude of the electric current applied by the third current generator 34 should be smaller than that of the electric current applied by each of the first current generators 14, 64 and by each of the second current generators 24, 74.

When the current density of the electric current applied by the third current generator is from about 0.5 $\mu A/cm^2$ to about 25 $\mu A/cm^2$, the antirust effect of the treated water 41 is capable of being determined promptly and accurately.

Then, the measurement and output devices 36 and 86 respectively measure the potential difference across the first cathode electrode 13 and the second cathode electrode 23 and the potential difference across the first comparative cathode electrode 63 and the second comparative cathode electrode 73. The larger the potential difference across the cathode electrodes, the larger the electrical resistance at the cathode electrodes, which means that films of calcium carbonate abundant in calcitic crystals are formed at the cathode electrodes.

The measurement and output devices 36 and 86 output and send the measured potential differences, respectively as an output signal A and an output signal B, to the determiner 91. The determiner 91 checks whether the ratio of the output signal A to the output signal B is more than 100%. When it is the case, the determiner 91 determines that the cathode electrodes 3 have a larger electrical resistance than the comparative cathode electrodes 53 and that the antirust effect of treated water 41 is enhanced.

The determination device 1 for determining antirust effect of treated water according to the present invention is capable of checking an improvement in the antirust effect of water by measuring electrical properties such as potential differences across the cathode electrodes 3 and across the comparative cathode electrodes 53. Thus it is not necessary to observe the inner surface of the piping 103 to check whether corrosion of metal on the inner surface of the piping 103 is controlled by the installation of a water treatment device 102. Therefore the user does not bother to stop the operation of the equipment or to drain water from the piping 103; this device enables the user to check whether a water treatment device 102 serves to improve the antirust effect easily and conveniently.

Furthermore, the determination device 1 for determining antirust effect of treated water according to the present invention is capable of expediting the cathode reaction that occurs in metal pieces immersed in water by the application of an electric current. Thus it does not take a long time period from a few months to several years from the installation of a water treatment device 102 in a piping to observe the progress of corrosion in order to determine the effectiveness of the device in controlling metal corrosion, but just a short period of several days to check an enhancement in the antirust effect of water.

In addition, the antirust effect of treated water may be determined by measuring the potential difference across the first cathode electrode and the second cathode electrode without using the third current generator 34. For example, the potential difference across the first cathode electrode 13 and the second cathode electrode 23 may be measured under the conditions where the magnitude of an electric current applied by the first current generator 14 is set to a value that is different from the magnitude of an electric current applied by the second current generator 24. Also, the magnitude of electric currents flowing through the cathode electrodes 3 may be controlled by changing the magnitude of an electric current applied by the first current generator 14 and the magnitude of an electric current applied by the second generator at regular intervals by means of the electric current changer 35. Furthermore, when the potential differences are used as output signals, the operation of the first and second current generators 14, 24, 64 and 74 should be controlled so that the magnitude of the electric current flowing through the first cathode electrode 13 and the second cathode electrode 23 is the same as that of the electric current flowing through the first comparative cathode electrode 63 and the second comparative cathode electrode 73.

We will further explain the invention by means of examples.

Working Example 1

Calcium sulfate was added to 5,000 mL of tap water so that the hardness of the water would be 300 ppm. Untreated water 42 was thus produced. Two pieces of hybrid ceramic, each of which was 13.5 mm in diameter and 19 mm in length, were placed in the untreated water 42. The hybrid ceramic pieces were the same as those incorporated into a device named "THE BIOWATER". The water with the two pieces of hybrid ceramic was allowed to stand for 15 minutes. Treated water 41 was thus produced. In this treated water 41 were immersed two anode electrodes 2 and two cathode electrodes 3 of a first potential difference measurement device 11 of a determination device for determining antirust effect of treated water 1. Also, in untreated water 42 were immersed two comparative anode electrodes 52 and two comparative cathode electrodes 53 of a second potential difference measurement device 61 of a determination device for determining antirust effect of treated water 1. An electrode with a surface of polished silver was used as each of the cathode electrodes 3 and 53, while a platinum-plated electrode was used as each of the anode electrodes 2 and 52. Each of the cathode electrodes 13, 23, 63, and 73 had a surface area of 0.2 cm$^2$.

Then, the first current generators 14 and 64 and the second current generators 24 and 74 were driven for 48 hours so that they would provide an electric current of 4 μA. The magnitude of the electric current applied by the first current generators 14 and 64 was 4 μA. After the 48 hours, the third current generator 34 and 84 were activated while the first current generators 14 and 64 and the second current generators 24 and 74 were kept operating. The third current generators 34 and 84 made an electric current of 0.5 μA flow through each of the cathode electrodes 3 and the comparative cathode electrodes 5. After 30 minutes from the activation of the third current generators 34 and 84, or after 48 hours and 30 minutes from the activation of the first current generators 14 and 64 and the second current generators 24 and 74, the magnitude of the electric current provided by the third current generators was changed every 30 minutes by electric current changers 35 and 85. A series of changes of the electric current was conducted on a one-hour cycle, beginning at the activation of the third current generators 34 and 84.

Since the magnitude of the electric current provided by the first current generators 14 and 64 and that of the electric current provided by the second current generators 24 and 74 are larger than the magnitude of the electric current provided by the third current generators 34 and 84, electric currents always flowed into the cathode electrodes 13, 63, 23, and 73 where the cathode reaction always occurred while the electric current was being provided by the third current generators 34 and 84.

Figure 5:
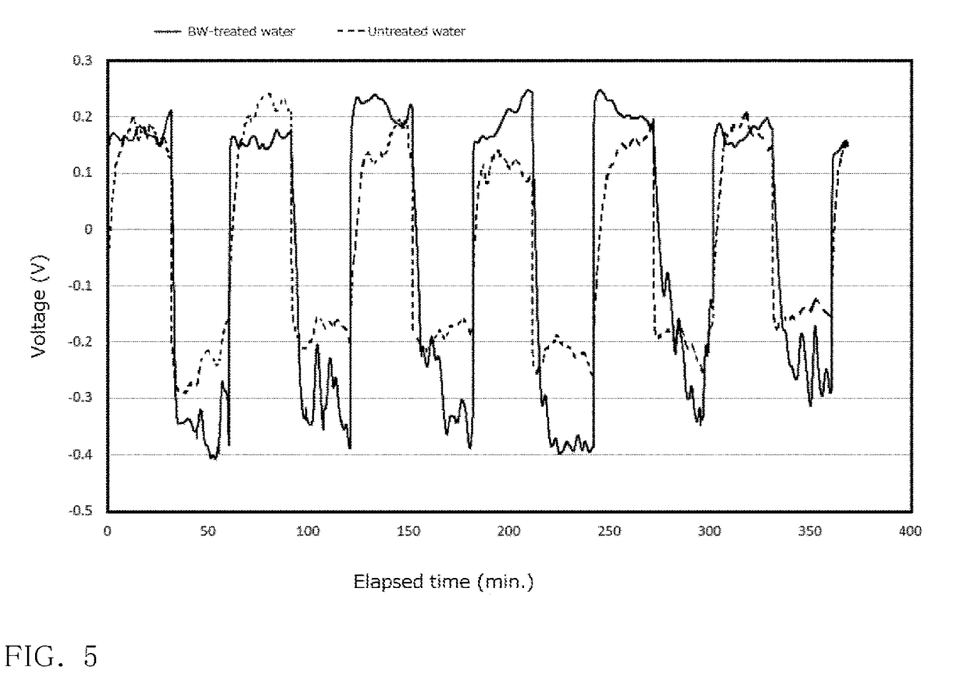
FIG. 5 is a graph showing how voltages measured in the working example changed with time.

While the third current generators 34 and 84 were providing the electric current, the potential difference across the first cathode electrode 13 and the second cathode electrode 23 and that across the first comparative cathode electrode 63 and the first comparative cathode electrode 73 were continuously measured. The results are shown in FIG. 5. The potential difference in the first half, or the first 30 minutes, of each cycle, had positive values, while the potential difference in the latter half, or the latter 30 minutes, of each cycle, had negative values. The average of the values of the potential difference in the first 30 minutes and that of the values of the potential difference in the last 30 minutes were respectively calculated. The results are shown in Table 1 below. In FIG. 5, the zero on the axis of abscissas, or the axis of the elapsed time, denotes the point when the operation of the third current generators 34 and 84 was begun.

In addition, the electrical resistance, which may be called "polarization resistance" hereinafter, of the cathode electrodes 3 or 53 was calculated for each cycle. The following equation was used for the calculation:

$$R_{p1} = (V_{1+} - V_{1-})/2I - R \quad (5)$$

$R_{p1}$: polarization resistance in each cycle
$V_{1+}$: average of the values of the potential difference in the first 30 minutes
$V_{1-}$: average of the values of the potential difference in the last 30 minutes
I: magnitude of the electric current that was made to flow through the cathode electrodes by the third current generator
R: resistance of the solution between the pair of cathode electrodes The resistance of the solution between the pair of cathode electrodes was automatically decided depending on the distance between the cathode electrodes and whether the solution had been treated or untreated.

In equation (5) above, the entire resistance is calculated according to "$(V_{1+} - V_{1-})/2I$". The subtraction of "R", the electrical resistance of the solution, from the entire resistance provides "$R_{p1}$", the electrical resistance of only the cathode electrodes.

The polarization resistance of each cycle and the average of the polarization resistances of all the cycles are shown in Table 1 below. In addition, the ratio of the average of the resistances of the cathode electrodes immersed in the treated water to the average of the resistances of the comparative cathode electrodes immersed in the untreated water was also calculated: The result was 137.5%.

TABLE 1

|  | 1$^{st}$ potential difference measurement device (for treated water) | | | 2$^{nd}$ potential difference measurement device (for untreated water) | | |
|---|---|---|---|---|---|---|
|  | Average voltage (mV) for +0.5 μA | Average voltage (mV) for −0.5 μA | Polarization resistance (kΩ) | Average voltage (mV) for +0.5 μA | Average voltage (mV) for −0.5 μA | Polarization resistance (kΩ) |
| 1$^{st}$ cycle | 170.58 | −350.51 | 519.00 | 159.01 | −241.88 | 398.80 |
| 2$^{nd}$ cycle | 157.22 | −298.26 | 453.37 | 203.36 | −179.57 | 380.84 |
| 3$^{rd}$ cycle | 216.44 | −279.99 | 494.33 | 138.55 | −184.84 | 321.30 |
| 4$^{th}$ cycle | 198.03 | −363.43 | 559.35 | 110.34 | −218.23 | 326.49 |
| 5$^{th}$ cycle | 210.01 | −207.42 | 415.32 | 130.57 | −200.00 | 328.48 |
| 6$^{th}$ cycle | 171.21 | −230.93 | 400.03 | 164.61 | −147.46 | 309.98 |
| Average |  |  | 473.56 (137.5%) |  |  | 344.32 (100%) |

As understood, the working example shows that the cathode electrodes 3 immersed in the treated water 41 has a large electrical resistance, compared with the comparative cathode electrodes 53 immersed in the untreated water 42. Therefore the experiments proved that the cathode reaction in the treated water 41 formed closer and more uniform films of calcium carbonate with a larger proportion of calcitic crystals than the cathode reaction in the untreated water 42 did. The formation of the calcium carbonate films controls metal corrosion. Thus it was proven that the treated water 41 had an enhanced antirust effect, compared with the untreated water 42.

EXPLANATION OF REFERENCE NUMERALS

1 determination device for determining antirust effect of treated water
2, 12, 22, 52, 62, 72 anode electrode
3, 13, 23, 53, 63, 73 cathode electrode
11 first potential difference measurement device
14, first current generator
24, 74 second current generator
34, 84 third current generator
35, 85 electric current changer
36, 86 measurement and output device
41 treated water
42 untreated water
61 second potential difference measurement device
91 determiner
92 power supply
93, 94 current transducer
95 control circuit
96 flip-flop controller
102 water treatment device
103 piping
104, 105 three-way valve

We claim:

1. A method for determining antirust effect of treated water comprising:
 applying an electric current between a first cathode electrode of a pair of cathode electrodes and at least one anode electrode, and between a second cathode electrode of the pair of cathode electrodes and the at least one anode electrode, wherein the first cathode electrode, the second cathode electrode, and the at least one anode electrode are immersed in treated water that has been treated with a water treatment device, wherein the treated water comprises calcium carbonate, and wherein the water treatment device comprises a hybrid ceramic that emits far-infrared rays;
 applying a comparative electric current between a first comparative cathode electrode of a pair of comparative cathode electrodes and at least one comparative anode electrode, and between a second comparative cathode electrode of the pair of comparative cathode electrodes and the at least one comparative anode electrode, wherein the first comparative cathode electrode, the second comparative cathode electrode, and the at least one comparative anode electrode are immersed in untreated water that has not been treated with the water treatment device, wherein the untreated water comprises calcium carbonate; and
 determining an antirust effect of the treated water based on a first potential difference across the first cathode electrode and the second cathode electrode, and a second potential difference across the first comparative cathode electrode and the second comparative cathode electrode.

2. The method according to claim 1, wherein the antirust effect of the treated water is determined based on a ratio of the first potential difference to the second potential difference.

3. The method according to claim 2, wherein the pair of cathode electrodes and the pair of comparative cathode electrodes have a surface made of silver, and the at least one anode electrode and the at least one comparative anode electrode have a surface made of platinum.

4. The method according to claim 1, wherein the pair of cathode electrodes and the pair of comparative cathode electrodes have a surface made of silver, and the at least one anode electrode and the at least one comparative anode electrode have a surface made of platinum.

5. The method according to claim 1, wherein the water treatment device contacts water with the hybrid ceramic which emits far-infrared rays having wavelengths from 4.4 µm to 15.4 µm at an integral emissivity of 92% or more.

6. The method according to claim 1, further comprising applying an electric current between the first cathode electrode and the second cathode electrode, and applying a comparative electric current between the first comparative cathode electrode and the second comparative cathode electrode.

7. The method according to claim 1, further comprising:
 installing the water treatment device within piping at a facility;
 operating the water treatment device at the facility to treat water that runs through piping at the facility; and
 collecting the water that has been treated by the water treatment device at the facility, wherein the water that has been treated by the water treatment device comprises the treated water.

8. The method according to claim 1, wherein determining the antirust effect of the treated water comprises:
 determining the antirust effect of the treated water without observing an inner surface of piping at a facility.

9. The method according to claim 1, further comprising:
 receiving a first output signal from a first electrical current measurement device based on the first potential difference across the first cathode electrode and the second cathode electrode;
 receiving a second output signal from a second electrical current measurement device based on the second potential difference across the first comparative cathode electrode and the second comparative cathode electrode;
 wherein determining the antirust effect of the treated water comprises:
  determining whether the antirust effect of the treated water is enhanced as compared to an antirust effect of the untreated water independent of stopping operation of the water treatment device based on a comparison of the first output signal and the second output signal.

10. The method according to claim 9, wherein the determining whether the antirust effect of the treated water is enhanced as compared to the antirust effect of the untreated water comprises:
 determining whether the first output signal is larger than the second output signal; and
 determining that the antirust effect of the treated water is enhanced as compared to an antirust effect of the untreated water based on determining that the first output signal is larger than the second output signal.

11. The method according to claim 10, wherein determining whether the first output signal is larger than the second output signal comprises:
 calculating a ratio of the first output signal to the second output signal.

* * * * *